(12) United States Patent
Hashim

(10) Patent No.: US 10,792,269 B2
(45) Date of Patent: Oct. 6, 2020

(54) GLYCERYL 3-HYDROXYBUTYRATES FOR MIGRAINE SYMPTOM MANAGEMENT

(71) Applicant: NeuroEnergy Ventures, Inc., New York, NY (US)

(72) Inventor: Sami Hashim, Dobbs Ferry, NY (US)

(73) Assignee: NeuroEnergy Ventures, Inc., New York, NY (US)

( * ) Notice: Subject to any disclaimer, the term of this patent is extended or adjusted under 35 U.S.C. 154(b) by 0 days.

(21) Appl. No.: 16/220,365

(22) Filed: Dec. 14, 2018

(65) Prior Publication Data

US 2019/0117612 A1    Apr. 25, 2019

Related U.S. Application Data

(63) Continuation of application No. 15/389,828, filed on Dec. 23, 2016, now abandoned.

(51) Int. Cl.
*A61K 31/225* (2006.01)

(52) U.S. Cl.
CPC .................................. *A61K 31/225* (2013.01)

(58) Field of Classification Search
CPC .................................................. A61K 31/225
See application file for complete search history.

(56) References Cited

U.S. PATENT DOCUMENTS

| | | | |
|---|---|---|---|
| 7,807,718 | B2 | 10/2010 | Hashim |
| 8,748,400 | B2 | 6/2014 | Henderson |
| 9,138,420 | B2 | 9/2015 | D'Agostino et al. |
| 9,364,456 | B1 | 6/2016 | Weeber et al. |
| 2012/0034193 | A1 | 2/2012 | Rees et al. |
| 2014/0072654 | A1 | 3/2014 | D'Agostino et al. |
| 2014/0073693 | A1 | 3/2014 | D'Agostino et al. |
| 2015/0231172 | A1 | 8/2015 | D'Agostino et al. |
| 2016/0067207 | A1 | 3/2016 | D'Agostino et al. |
| 2016/0078782 | A1 | 3/2016 | Meidenbauer |
| 2016/0317487 | A1 | 11/2016 | D'Agostino et al. |
| 2017/0000754 | A1 | 1/2017 | Weeber et al. |
| 2017/0196827 | A1 | 7/2017 | Veech et al. |
| 2017/0258745 | A1 | 9/2017 | Millet |
| 2017/0266148 | A1 | 9/2017 | D'Agostino et al. |
| 2017/0290792 | A1 | 10/2017 | Cavaleri |
| 2017/0296501 | A1 | 10/2017 | Lowery |

FOREIGN PATENT DOCUMENTS

| | | |
|---|---|---|
| FR | 2997302 | 5/2015 |
| WO | 2017011294 A1 | 1/2017 |
| WO | 2018009208 A1 | 1/2018 |
| WO | 2018049383 A1 | 3/2018 |
| WO | 2018115158 A1 | 6/2018 |

OTHER PUBLICATIONS

Balietti et al; Ketogenic diets: An historical antipiletic therapy with promising potentiualities for the aging brain; Aging Research and Reviews 9 (2010) 273-279.
Bengsch; Less Garbs, more fat: ketogenic diet makes migraine patient's headaches disappear; Oct. 14, 2016.
Cahill; President's address: Starvation; Trans Am Clin Climatol; Assoc 94:1-21, 1983.
Clarke et al; Kinetics, safety and tolerability of (R)-3-hydroxybutyryl (R)-3-hydroxybutyrate in healthy adult subjects; Regul Toxicol Pharmacol 63: 401-408, 2012.
Di Lorenzo, et la; Cortical function correlates of responsiveness to short-lasting preventive intervention with ketogenic diet in migraine: a multimodal evoked potential study; J Headache Pain 17: 58-67, 2016.
Di Lorenzo et al; Diet transiently improves migraine in two sisters: possible role of ketogenesis?; Funct. Neurol. Oct.-Dec. 2013; 23 (4):305-308 Published online at https:/www.ncbi.nlm.nih.gov/pmc/articles/PMC3951260/.
Di Lorenzo et al; Migraine improvement during short lasting ketogenesis: a proof-of-concept study; European J Neurology 2015, 22:170-177.
Faul et al; Traumatic Brain Injury in the United States: Emergency Department Visits, Hospitalizatiojns and Deaths 2002-2006.; Centers for Disease Control and Prevention National Center for Injury Prevention and Control, Atlanta, GA (Mar. 2010); http://www.cdc.gov/TraumaticBrainInjury/.
Fuehrlein, et al; Differential metabolic effects of saturated versus polyunsaturated fats in ketogenic diets; J Clin Endocrinol Metab 89:1641-1645, 2004.
Gasier et al; Neuroprotective and disease-modifyingeffects of the ketogenic diet; Behav. Pharmacol Sep. 17, 2006 (5-6) 431-439.
Hashim et al; Ketone body therapy: from the ketogenic diet to the oral administration of ketone ester; J Lipid Res 55:1818-1826, 2014.
Huttenlocher, et al; Medium-Chain triglycerides as a therapy for intractable childhood epilepsy; Neurology, vol. 11, Nov. 1971, 1097-1103.
Institute of Medicine Report, Nutrition and Traumatic Brain Injury, Improving Acute and Subacute Health Outcomes in Military Personnel, Apr. 2011; at www.iom.edu/tbinutrition.
International Search Report and Written Opinion of the International Search Authority dated Feb. 2, 2018 in PCT/US2017/063832 filed Nov. 30, 2017. (11 pages).
Kossoff, et al; Ketogenic Diets: New Advances for Metabolism-Based Therapies; Curr Opin Neurol. Apr. 2012; 25(2): 173-178. doi:10.1097/WCO.0b013e3283515e4a.
Newport et al; A new way to produce hyperketonemia: Use of ketone ester in a case of Alzheimer's disease; Alzheimer's and Dimentia 2014: 1-5, Elsevier.
Prins et al; The collective potential of cerebral ketone metabolism in traumatic brain injury; J Lipid Res 55:2450-2457, 2014.
Prins et al; Increased cerebral uptake and oxidation of endogenous beta HB improves ATP following traumatic brain injury; J Neurochem 90: 666-672, 2004.
Rainero et al; Insulin Sensitivity is impaired in patients with migraine; Cephalagia 25:593-597, 2005 (Abstract).
Ritter et al; Evaluation of a carbohydrate-free diet fir patients with severe head injury; J Neurotrauma 13: 475-485, 1996.

(Continued)

*Primary Examiner* — James D. Anderson
(74) *Attorney, Agent, or Firm* — Irving M. Fishman

(57) ABSTRACT

A method of management of migraine symptom reduction and/or management and/or prophylaxis is disclosed using 3-hydroxybutyrate glycerides is disclosed.

14 Claims, No Drawings

(56) References Cited

OTHER PUBLICATIONS

Salame et al—Ketogenic neuroprotection of Repeat TBI in Juvenile Rats—J Neurotrauma 2012 Abstract.
Teasdale; Assessment of Coma and Impaired Consciousness: A Practical Scale; The Lancet, Jul. 13, 1974, pp. 81-84.
Vanltallie, et al; Ketone metabolism's ugly duckling; Nutr Rev 61:327-341, 2003.
Wilberger; Sports Related Concussion; MerckManual Professional Version online at http://www.merck.manuals.com/professional/injuries-poisining/traumatic-brain-injury-tbi/sports-related-concussion last full revision Oct. 2013.
Wilberger; Traumatic Brain Injury; Merck Manual Professional Version online at http://www.merckmanuals.com/professional/injuries-poisoning/traumatic-brain-injury-tbi/fraumatic-brain-injury last full revision Oct. 2013.
Wu, et al; Medium-Chain Triglycerides in Infant Formulas and their relation to Plazma Ketone Body Concentrations; Pediatric Research, vol. 20, No. 4, 338-341, 1986.
Wilder; The Effectof Ketonemia on the Course of epilepsy; The Clinic Bulletin, vol. 2, No. 307, Jul. 27, 1921.
Larry Mccleary et al: Migraine Headaches—Rethinking an Old Malady; Brain Blogger; retrieved from Internet: URL:https://www.brainblogger.com/2008/01/28/rethinking-an-old-malady/.

GLYCERYL 3-HYDROXYBUTYRATES FOR MIGRAINE SYMPTOM MANAGEMENT

CROSS-REFERENCE TO RELATED APPLICATIONS

Not Applicable.

STATEMENT REGARDING FEDERALLY SPONSORED RESEARCH OR DEVELOPMENT

Not Applicable

FIELD OF THE INVENTION

The present invention is directed to the field of migraine headaches and the management of the symptomology thereof. The invention further relates to the field of ketone bodies and further to ketone bodies in the form of 3-hydroxybutyrate glycerides.

BACKGROUND OF THE INVENTION

Migraine headache is among the most prevalent of headache related disorders. It affects up to 5% of the population and is more common in women than in men. Despite advances in the pathophysiology of migraine, commonly available preventive measures are only partially effective and come with some serious adverse side effects. Note especially in this regard the ergot alkaloids and their analogs. In recent years, there has been increasing interest in the role of diet in the prevention and treatment of migraine headache. Rainero et al, *Insulin sensitivity is impaired in patients with migraine*, Cephalagia 25:593-597, 2005, reported on twins with a high frequency of migraine headaches who improved during a ketogenic diet. The authors ascribe the pathogenesis of migraine headache to diminished insulin sensitivity in the brain with consequent diminished utilization of glucose as a source of energy. Rainero states: "Our data show that insulin sensitivity is impaired in migraine and suggest a role for insulin resistance in the comorbidity between migraine and vascular disease."

The ketogenic diet involves severe restriction of carbohydrates and includes a high proportion of fats. The first ketogenic diet was published in 1921 by Wilder (*The effects of ketonemia on the course of epilepsy*, Mayo Bull 2:307-308, 1921) relating to the treatment of children with epilepsy that is resistant to the then available pharmacologic therapies. In terms of energy distribution, the original ketogenic diet was 90% fat, 8% protein, and 2% carbohydrate.

The ketogenic diet mimics the metabolic state of total starvation. Both result in hyperketonemia of approximately the same degree, with blood ketone body levels of 2-7 mM (Cahill, *President's address: Starvation*; Trans Am Clin Climatol Assoc, 94:1-21, 1983). It is important to emphasize that this degree of hyperketonemia is fully buffered in the circulation, does not induce acidosis, and has been termed as "physiologic" or "therapeutic" ketosis (Hashim, et al; *Ketone body therapy: from the ketogenic diet to the oral administration of ketone ester*; J Lipid Res 44:1818-1826, 2014).

More recently, the ketogenic diet was used in the treatment 25 chronic, repetitive migraine patients (DiLorenzo, et al; *Cortical function correlates of responsiveness to short-lasting preventive intervention with ketogenic diet in migraine: a multimodal evoked potential study*, J Headache Pain 17: 58-67, 2016). (Chronic, repetitive migraine patients, after presenting with a first migraine episode generally lasting 4-72 hours also present with an additional episode in less than 4 days after the initiation of the prior episode, with many having as many as 15 or more episodes per month. "Episodic migraines" present as apparently discrete migraines separated by more than 72 hours.) Moreover, in order to investigate whether the ketogenic diet had prophylactic effects in migraine, the authors evaluated, for the first time, the influence of the diet for one month on the habituation of visual and somatosensory cortical evoked potentials in a group of patients with episodic migraine. After one month on the diet, there was a significant reduction in the mean attack frequency and duration of migraines. The authors conclude that the ketogenic diet acts on regulating the balance between excitation and inhibition at the cortical level, through induction of neural plasticity and enhancements in brain energy metabolism. However, there is no clear understanding of the mechanism of action presented.

The ketogenic diet is not the most pleasant of diets. It is rather difficult to follow, and when followed, it can produce rises in LDL cholesterol, in uric acid, and free fatty acids. Occasionally, the ketogenic diet may result in increased incidence of nephrolithiasis and other serious complications (Van Itallie, et al; *Ketone metabolism's ugly duckling*; Nutr Rev. 61:327-341, 2003). Some of these adverse effects can be prevented by ensuring adequate hydration; and the hyperlipidemia can be avoided by boosting the proportion of polyunsaturated and monounsaturated fats in the diet (Fuehrlein et al *Differential metabolic effects of saturated versus polyunsaturated fats in ketogenic diets*; J Clin Endocrinol Metab 89:1641-1645, 2004). Also, the inclusion of medium-chain triglycerides (glycerol esters of fatty acids having typically 8 and/or 10 carbons in the fatty acid groups) into the ketogenic diet may improve the tolerability of the ketogenic diet (Huttenlocher et al; *Medium-Chain triglycerides as a therapy for intractable childhood epilepsy*, Neurology, Vol 11, November 1971, pp 1097-1103; Wu et al, *Medium-Chain Triglycerides in Infant Formulas and their Relation to Plasma Ketone Body Concentrations*, Pediatric Research, Vol 20, No. 4, pp 338-341, 1986; Balietti et al, *Ketogenic diets: An historical antiepileptic therapy with promising potentialities for the aging brain*, Aging Research and Reviews 9 (2010) 273-279.

OBJECTS OF THE INVENTION

An object of the invention is to provide a method of managing one or more of the symptoms of migraine headache in a subject in need thereof without the need for current drug therapies such as ergot alkaloids.

Another object of the invention is to provide a method of managing one or more of the symptoms of migraine headache in a subject in need thereof as a supplement to treatment with other therapeutic treatments for migraine.

A further object of the invention is to provide a method of managing one or more of the symptoms of migraine headache in a subject in need thereof without the need to resort to a ketogenic diet.

An object of the invention is to provide a method of treating one or more of the symptoms of migraine headache in a subject in need thereof without the need for current drug therapies such as ergot alkaloids.

Another object of the invention is to provide a method of treating one or more of the symptoms of migraine headache in a subject in need thereof as a supplement to treatment with other therapeutic treatments for migraine.

A further object of the invention is to provide a method of treating one or more of the symptoms of migraine headache in a subject in need thereof without the need to resort to a ketogenic diet.

An object of the invention is to provide a method of preventing one or more of the symptoms of migraine headache in a subject in need thereof without the need for current drug therapies such as ergot alkaloids.

Another object of the invention is to provide a method of preventing one or more of the symptoms of migraine headache in a subject in need thereof as a supplement to treatment with other therapeutic treatments for migraine.

A further object of the invention is to provide a method of preventing one or more of the symptoms of migraine headache in a subject in need thereof without the need to resort to a ketogenic diet.

An object of the invention is to provide a method of preventing one or more of the symptoms of migraine headache in a subject having a history of episodic migraine without the need for current drug therapies such as ergot alkaloids.

Another object of the invention is to provide a method of managing one or more of the symptoms of migraine headache in a subject having a history of episodic migraine as a supplement to treatment with other therapeutic treatments for migraine.

A further object of the invention is to provide a method of managing one or more of the symptoms of migraine headache in a subject having a history of episodic migraine without the need to resort to a ketogenic diet.

An object of the invention is to provide a method of preventing one or more of the symptoms of migraine headache in a subject having a history of chronic repetitive migraine without the need for current drug therapies such as ergot alkaloids.

Another object of the invention is to provide a method of managing one or more of the symptoms of migraine headache in a subject having a history of chronic repetitive migraine as a supplement to treatment with other therapeutic treatments for migraine.

A further object of the invention is to provide a method of managing one or more of the symptoms of migraine headache in a subject having a history of chronic repetitive migraine without the need to resort to a ketogenic diet.

Still another object of the invention is to achieve the forgoing objects by administration of a 3-hydroxybutyrate-glyceride ester in an amount of the 3-hydroxybutyroyl

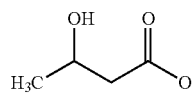

content corresponding to the oral administration of about 0.5 g/kg to 2.0 g/kg of body weight per day of glyceryl tris(3-hydroxybutyrate)

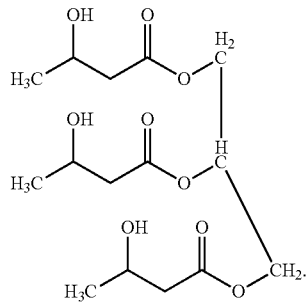 [SMILES: CC(O)CC(=O)OCC(COC(=O)CC(C)O)OC(=O)CC(C)O]

An even further object of the invention is to achieve the foregoing objects by administration of a 3-hydroxybutyroyl-glyceride ester in an amount so as to result in a total ketone body blood level of about 2 to about 7.5 mM.

Yet another object of the invention is to achieve the forgoing objects by administration of the glyceryl-(3-hydroxybutyrate) ester(s) in a regimen of 2-3×/day for at least 3 days for those with episodic migraine and 2-3 times/day for longer periods determined on the basis of the patient's history of duration of the chronic symptoms plus an additional 4 days.

Even further objects of the invention will become apparent to those of ordinary skill in the art after having benefit of the instant application.

BRIEF SUMMARY OF THE INVENTION

In brief, the foregoing objects of the invention and others can be obtained by the administration of a glyceryl-(3-hydroxybutyrate) ester to a subject who is having or has recently had a migraine headache or to one who is prone to migraine headaches. When the ester is glyceryl tris(3-hydroxybutyrate), it is administered in an amount that is typically in the range of 0.5 g/kg to 2.0 g/kg body weight per day in 2-3 divided doses, which for a 60-kg female is about 10-40 g/serving thrice daily to about 15-60 g/serving twice daily and for a 70 kg male is about 12-47 g/serving thrice daily to about 17.5-70 g/serving twice daily. These doses and serving sizes are designed to result in total ketone body blood levels (combined 3-hydroxybutyrate and acetoacetate) blood levels of 2-7.5 mM in an average typical subject to whom these compounds are administered. Those of ordinary skill in the art will know how to adjust these dosage amounts in subjects presenting with non-typical distribution and/or metabolisms such that the foregoing doses do not result in the blood level being in the correct range. When the ester is one of the other esters discussed more fully below, the dose is calculated to deliver a comparable amount of the 3-hydroxybutyroyl moiety that is ultimately delivered by the glyceryl tris(3-hydroxybutyrate) administered as stated above.

BRIEF DESCRIPTION OF THE DRAWING

Not Applicable

DETAILED DESCRIPTION OF THE INVENTION

The present invention is directed to the use of compounds that have the 3-hydroxybutyroyl group

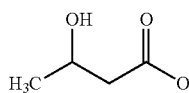

esterified to a glycerol group in the management, treatment, or prevention of one or more of the symptoms associated with migraine headache and/or management, treatment, or prevention of the underlying neurological basis for the symptoms. For the present invention purposes, treatment is intended to mean that administration is during an episode of migraine symptoms; prevention is intended to mean administration of the ester to a subject known to have migraine headaches and is prone to the same, especially prone to having multiple episodes (which may be as few as 1 within about 72 hours of the onset of a prior episode initiation and as frequent as more than 15 episodes or more within a month), and additionally "prone to" is intended to include, without limitation, those having a history of migraines after a known or suspected precipitating event, where the lag time between the known or suspect precipitating event and the presentation of symptoms being determined from the individual's own history or a generally recognized association in the art. The esters can be those in which 3-hydroxybutyroyl groups

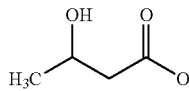

esterify 1, 2, or all 3 of the hydroxy groups in a single glycerol molecule. When less than all three of the glycerol hydroxy groups are esterified by the 3-hydroxybutyroyl group, the remaining glycerol hydroxy groups can remain unesterified, be esterified by omega-3-fatty acids, omega-6-fatty acids, omega-3,6-fatty acids, medium-chain fatty acids or mixtures thereof (Medium-chain fatty acids are fatty acids having carbon chains of generally 8 and/or 10 carbons, such as for example, one such medium-chain fatty acid in a purified form is caprylic acid.) Each 3-hydroxybutyroyl group in each molecule is independently in either D or L form and the bulk compound being administered can be a mix of any or all of the same (i.e. a mix of compounds having (a) all of the groups in the D form, (b) all of the groups in the L form, (c) some in the D-form and some in the L-form, (d) as well as mixtures of compounds selected from (1) a and b, (2) a and c, and (3) a, b, and c). Both the D and L forms of the 3-hydroxybutyroyl groups are active, however, the L form is utilized more slowly and thus, it is preferable that the 3-hydroxybutyroyl groups are substantially all in the D form. In a particularly preferred embodiment, about 90% to 98%, more preferably about 96% of the 3-hydroxybutyroyl groups are in the D form. Nonetheless, utilization of other amounts of D vs L forms are within the invention and can be selected from 100% D to 100% L and any mixture of D and L forms in any proportions. In addition, mixtures of esters having one, two, or 3 (3-hydroxybutyryl) groups with (a) no other esterification or (b) further esterification with an omega fatty acid (either 3-omega, 6-omega, or 3,6-omega or mixtures thereof) or (c) further esterified with a mid-chain fatty acid or mixtures of different mid-chain fatty acids or (d) further esterified with both an omega fatty acid and a mid-chain fatty acid are also contemplated to be within the scope of compounds for use in the present invention. A highly preferred embodiment is one in which the compound utilized for the present invention is glyceryl tris(3-hydroxybutyrate); an even more highly preferred compound is glyceryl tris(DL 3-hydroxybutyrate), the DL referring to the bulk compound and not necessarily a mixture in a specific molecule; and a still more highly preferred embodiment is in the use of glyceryl tris(D96%/L4% 3-hydroxybutyrate), D96%/L4% referring to the bulk compound and not necessarily a mixture in a specific molecule. These compounds and a method of manufacture thereof are described more fully in U.S. Pat. No. 7,807,718, which is incorporated herein concerning the description of the compounds and their manufacture.

In brief, the foregoing object of the invention and others can be obtained by the administration of a glyceryl-(3-hydroxybutyrate) ester to a subject who is having or has recently had a migraine headache or to one who is prone to migraine headaches. When the ester is glyceryl tris(3-hydroxybutyrate), it is generally orally administered in an amount that is typically in the range of 0.5 g/kg to 2.0 g/kg body weight per day (more specifically 0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.1 g/kg, 1.2 g/kg, 1.3 g/kg, 1.4 g/kg, 1.5 g/kg, 1.6 g/kg, 1.7 g/kg, 1.7 g/kg, 1.8 g/kg, 1.9 g/kg, or 2 g/kg, as well as amounts intermediary between any of these specifically recited amounts) in 2-3 divided doses, which for a 60 kg female is about 10-40 g/serving (more specifically 10 g/serving, 12.5 g/serving, 15 g/serving, 17.5 g/serving, 20 g/serving, 22.5 g/serving, 25 g/serving, 30 g/serving, 35 g/serving, 40 g/serving as well as amounts intermediary between any of these specifically recited amounts) thrice daily (approximately every 8 hours) to about 15-60 g/serving (more specifically 15 g/serving, 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, or 60 g/serving as well as amounts intermediary between any of these specifically recited amounts) twice daily (approximately every 12 hours) and for a 70 kg male is about 12-47 g/serving (more specifically 12 g/serving, 15 g/serving, 17.5 g/serving, 20 g/serving, 22.5 g/serving, 25 g/serving, 30 g/serving, 35 g/serving, 40 g/serving, 45 g/serving, 47 g/serving, as well as amounts intermediary between any of these specifically recited amounts) thrice (approximately every 8 hours) daily to about 17.5-70 g/serving (more specifically 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, 60 g/serving, 65 g/serving, 70 g/serving, as well as amounts intermediary between any of these specifically recited amounts) twice (approximately every 12 hours) daily. These doses and serving sizes are intended to result in total ketone body blood levels (combined 3-hydroxybutyrate and acetoacetate) blood levels of 2-7.5 mM (more specifically 2 mM, 2.25 mM, 2.5 mM, 2.75 mM, 3 mM, 3.25 mM, 3.5 mM, 4 mM, 4.25 mM, 4.5 mM, 4.6 mM, 4.7 mM, 4.8 mM, 4.9 mM, 5.0 mM, 5.1 mM, 5.2 mM, 5.3 mM, 5.4 mM, 5.5 mM, 5.6 mM, 5.7 mM, 5.8 mM, 5.9 mM, 6.0 mM, 6.1 mM, 6.2 mM, 6.3 mM, 6.4 mM, 6.5 mM, 6.6 mM, 6.7 mM, 6.8 mM, 6.9 mM, 7.0 mM, 7.1 mM, 7.2 mM, 7.3 mM, 7.4 mM, 7.5 mM as well as intermediary levels between any of these specifically recited levels and any of these may serve as a lower end of a range or upper end of a range provided the upper end of the range is larger than the lower end of that range) in an average typical subject to whom these compounds are administered. (Acetoacetate is an oxidized form of 3-hydroxybutyrate in which the 3-hydroxy group is replaced by a 3-oxo group

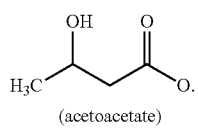
(acetoacetate)

When the esters used in the present invention are ingested orally, the esters are primarily hydrolyzed in the intestinal tract due to pancreatic lipase, releasing the 3-hydroxybutyrate moiety which is absorbed, and the body utilizes the 3-hydroxybutyrate by converting it to acetoacetate which, in turn, is actually used by the cells.) Those of ordinary skill in the art will know how to adjust these dosage amounts in subjects presenting with non-typical distribution and/or metabolisms such that the foregoing doses do not result in the blood level being in the correct range. When the ester is one of the other esters discussed more fully below, the dose is calculated to deliver a comparable amount of the 3-hydroxybutyroyl moiety that is ultimately delivered by the glyceryl tris(3-hydroxybutyrate).

In the present specification, in any case where a range of values for a particular parameter is given and a more specific recitation of values within such range is given each specific value can be the basis for a new range limit as long as the lower limit is in fact less than the upper limit. By way of example, in the foregoing paragraph, the dosage range is given as "0.5 g/kg to 2.0 g/kg" with a more specific recitation of "0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.1 g/kg, 1.2 g/kg, 1.3 g/kg, 1.4 g/kg, 1.5 g/kg, 1.6 g/kg, 1.7 g/kg, 1.8 g/kg, 1.9 g/kg, or 2 g/kg". Based thereon, any of the more specific recited amounts may be the lower limit of a new range and any larger specific recited amount may be the upper limit of that new range and each such constructed range shall be deemed as specifically recited in this specification. As such the ranges of 0.5 to 0.6; 0.55 to 1.9, 0.75 to 1.7, 1.8 to 1.9, etc. are all deemed recited herein. The same is applicable to the other parameters relating to dosages based on body weight, serving sizes, etc. as well.

The constellation of symptoms typically associated with migraine headaches includes transient visual and/or gastrointestinal disturbances. The headache is often preceded by a visual aura of flashing moving dots or scintillating lines partly obscuring vision, discrete areas of loss of vision, blurring of vision, and/or photophobia ("prodromal disturbances"). These prodromal disturbances last between 5-30 minutes and are followed by the headache (usually unilateral) which may last for 4 to 72 hours. The present invention is directed to relief of the headache entirely; reduction of the presentation of the headache in its frequency of appearance and/or its intensity of presentation; and prevention of its presentation in one in whom it is known to appear or one in whom migraine headaches have previously appeared after a known or suspected precipitating event. Generally, the patient's own history and the patient's own association of an event or stimulus with the onset of a migraine headache is relied upon for identification of a "suspect precipitating event" as these are not well characterized for the general population of migraineurs. The appearance of one or more of the prodromal symptoms (mentioned further elsewhere in this specification) are generally considered cues for initiating 3-hydroxybutyrate ester therapy, but these are "associated" symptoms, rather than "precipitating events. The "treatment", "prevention", "reduction of frequency", and/or "reduction of intensity" is of at least one of the headache itself, and/or the gastrointestinal disturbances, and/or the visual effects, and/or the photophobia symptoms that may accompany the headache, and generally is more specifically applicable to at least the headache and preferably the headache and one or more of these associated symptoms. While the treatment, reduction of frequency, or reduction of intensity of the prodromal symptoms usually preceding the headache may simultaneously be achieved, they are not required as part of the present invention. However, in the absence of a recognition of any other reason to initiate a round of administration of the glyceryl-(3-hydroxybutyrate) esters, the presentation of one or more of the prodromal symptoms can be used as a cue to initiate such administration or if already having initiated administration to perhaps increase the amount being administered.

The ester compounds for use in the present invention are administered in amounts that deliver the same amount of 3-hydroxybutyroyl moiety as that when 0.5 g/kg to 2.0 S/kg body weight of the glyceryl tris(3-hydroxybutyrate) is administered orally. Again, the focal point is to achieve the appropriate ketone body (3-hydroxybutyroyl level plus acetoacetate level) in the blood of between 2 mM and 7 mM, preferably 4.5 mM to 7 mM, more preferably 5 mM to 7 mM. In cases where the actual volume or weight of this amount is too cumbersome or undesired to give as a single dose, the dose can be divided into multiple divided doses of desirable size given multiple times per day or in multiple dosage units given in a single dose (i.e. within a few moments of one another as desired). Preferably the dose is divided into 2-3 divided doses, spaced apart approximately equally over the course of a 24-hour period, so that twice daily dosing is approximately every 12 hours and thrice daily dosing is approximately every 8 hours. By way of example, if 50 g is desired to be administered, it can be done as a single dose of 50 g in a single dosage form or distributed in a food or drink or it can be administered in ½ such amounts twice daily, or it can be administered in a dosage form having ½ the dose in two dosage units given within a few moments of one another (preferably within a few seconds of one another when a substantially single dosing is desired). Where multiple dosings per day are desired or multiple dosage units per day at a single dosing are desired, other fractional dosings and multiple dosage units will be known to those of ordinary skill in the art and include without limitation administration of ⅓ the above amounts administered 3 times a day or in three units administered at substantially the same time; ¼ the above amounts administered 4 times a day or in four units administered at substantially the same time or 2 units twice in a day. The intent and objective is to induce a therapeutic hyperketonemia characterized by blood levels of the 3-hydroxybutyroyl group

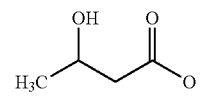

of 2 mM-7.5 mM, (such as 4.5 mM, 5.0 mM, 5.5 mM, 6.0 mM, 6.5 mM, 7.0 mM or 7.5 mM, and all mM levels between any particular of these explicitly recited amounts is deemed to be explicitly disclosed as well) comparable to those achieved by ketogenic diet or starvation. Those of ordinary skill in the art will appreciate other variations on the theme.

Generally, upon oral administration, the necessary blood ketone body levels can be achieved within 24 hours, more usually within 12 hours, even more typically within 6 hours, even more typically within 2 hours, yet more likely within 1 hour. On oral administration, the ketone body blood levels rise quickly and peak in about 30 minutes or 45 minutes to 1 hour. Once administration has begun due to the presentation of (a) a migraine headache or (b) a presentation of a subset of migraine headache symptoms, (c) a presentation of one or more migraine headache prodromal symptoms, or (d) recognition of the occurrence of a migraine headache precipitating event or recognition of the occurrence of a migraine headache suspect precipitating event has occurred, administration should continue on a daily basis for 2, 3, or 4 days in the case of a subject one knows or believes to be an episodic migraine subject or in the case of a subject known to have chronic repetitive migraines, for up to a month, and longer after the last repetitive migraine in a particular cluster. In the case of the chronic repetitive migraine subject, the patient's history as to how long the bouts of repetitive migraine last (i.e. without limitation, 2 weeks, 3 weeks, 4 week, etc) can be used as a guide to how long dosing should continue, which should be at least 4 days beyond the last expected migraine in a series. For example, without being limited thereto, a subject having a history of chronic repetitive migraines that begin on day 1, last a couple of days and repeat in roughly 4 days' time, and continue to repeat for 2 weeks so that the last expected migraine starts on day 15, administration should continue at least through 19, and probably for a day or two longer. In the situation where one has a history of migraines presenting after a specific event, administration should be from as soon as possible after the occurrence of the known event linked to the onset of symptoms until at least 4 or more days after the usual appearance of the migraine symptoms associated with the event. In the situation where a subject has a history of approximately regular follow up migraine occurrences after an earlier one at somewhat regular intervals, administration should be begun from a point in time before the repeat migraine headache is anticipated to occur through at least 4 days after the expectation of such anticipated follow-up migraine. In the present invention, prophylactic (preventative) use of the glyceryl (3-hydroxybutyrate) esters to prevent migraine symptoms is generally directed to these last two situations. In the situation where the subject presents with the prodromal symptomology of a migraine, administration should begin as soon as possible and last as indicated above for the episodic subject or the chronic, repetitive subject as indicated above, but due to the short duration between prodromal symptomology presentation and headache onset, once prodromal symptoms have begun the administration is considered treatment and not prevention.

As previously stated, the above dosing range of the glyceryl tris(3-hydroxybutyrate) is expected to provide a total ketone body blood level (3-hydroxybutyroyl group

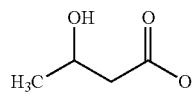

and acetoacetate) of 2 mM to 7 mM.

EXAMPLES

The following examples exemplify, but do not limit, the present invention.

Example 1

A 60 kg female presents with episodic migraines occurring one such headache occurring and then not again for a number of months. At each event, shortly before the headache begins, the subject has visual disturbances classic of migraine. The subject is requested to self-administer 15 grams of glyceryl tris(3-hydroxybutyrate) upon noticing the next time visual disturbance of this type appear and continue to do so 3 times a day for 4 days. The subject notices such symptoms, and ingests 15 g of glyceryl tris(3-hydroxybutyrate) within minutes of noticing the symptoms. The headache that follows is of lesser duration and lesser intensity than past episodes.

Example 2

A 70 kg male presents with chronic repetitive migraine where past history shows once a repetitive episode begins, the subject has a first migraine that lasts on average of 24 hours and another one arises in 2-3 days with this pattern continuing for about 30 days after which the migraines subside for 1 to 2 months and the cycle repeats again. There is no known or suspect event triggering these events. The subject is instructed to self-administer 20 g of glyceryl tris(3-hydroxybutyrate) upon the onset of the migraine and to continue to self-administer at this dosage 3 times a day for 35 days. The usual initial migraine is less severe and of shorter duration than past history occurrences. The repetitive migraines are further reduced in frequency and intensity than past history would suggest.

Example 3

The subject of Example 2 discontinues the administration after 35 days, is migraine free for two months and a further episode occurs and Example 2 is followed again, counting the start of this second migraine as day 1, except that after ceasing the administration on day 35, the subject begins administration again on day 90 (about 5-6 days before an expected onset of a further migraine based on this subject's history) and continues administration for an additional 40 days (that is for days 90 to 130). While expecting a migraine to occur on or about days 94-95, no such migraine appears then or throughout the period of administration ending on day 130.

Example 4

A 60 kg female presents with chronic repetitive migraine with a similar repetitive pattern to the male subject of Examples 2 and 3. She is instructed to self-administer 15 g of glyceryl tris(3-hydroxybutyrate) upon the onset of the migraine, rather than the 20 g as in Examples 2 and 3, but otherwise to follow the regimen in Examples 2 and 3. Similar relief to that shown in Examples 2-3 results.

The invention claimed is:
1. A method of use of a glyceryl (3-hydroxybutyrate) ester compound in the management of migraine symptomology comprising:

orally administering an amount of said compound, which, upon being hydrolyzed, gives rise to glycerol and 3-hydroxybutylate moieties,
- (a) to a subject presenting with at least one migraine symptom, wherein said amount is sufficient to eliminate, control, limit, or reduce said at least one symptom or
- (b) to a subject so as to prevent the onset of at least one of said symptoms from a previously established pattern of migraine symptom onset, said amount of said compound which is administered is sufficient to raise the subject's ketone body blood plasma levels, as measured by the subject's combined blood plasma levels of 3-hydroxybutyrate and acetoacetate, to a range having a lower and upper limit selected from 6 mM, 6.5 mM, 7 mM and about 7.5 mM within the first 24 hours of administration of said glyceryl (3-hydroxybutyrate) ester compound, provided said upper limit of the range is larger than the lower limit of the range.

2. The method of claim 1 wherein said compound is a glyceryl tris (3-hydroxybutyrate), a glyceryl bis (3-hydroxybutyrate), a glyceryl mono (3-hydroxybutyrate), or a mixture thereof, wherein each 3-hydroxybutyrate group is independently selected from D and L forms thereof, and wherein the compound is administered in a serving size of at least 0.5 g/kg body weight/day.

3. The method of claim 1 wherein said compound is
- (a) glyceryl tris (3-hydroxybutyrate) or
- (b) bulk glyceryl tris (3-hydroxybutyrate) (Bulk Tris Ester)

wherein each 3-hydroxybutyrate group is independently in the D or L form and wherein said Bulk Tris Ester is primarily glyceryl tris (3-hydroxybutyrate) with additional 3-hydroxybutyrate esters of glycerol, such that upon hydrolysis of said Bulk Tris Ester, there are, on average, three 3-hydroxybutyrate moieties for each glycerol moiety in said Bulk Tris Ester.

4. The method of claim 3 wherein said glyceryl tris (3-hydroxybutyrate) is selected from the group consisting of glyceryl tris (D-3-hydroxybutyrate), glyceryl tris (L-3-hydroxybutyrate), glyceryl tris (DL-3-hydroxybutyrate), and mixtures thereof, wherein the designation "DL" refers to the overall bulk of hydroxybutyrate groups and includes, but is not limited to any specific molecule.

5. The method of claim 3 wherein the glyceryl tris (3-hydroxybutyrate) is glyceryl tris (DL-3-hydroxybutyrate).

6. The method of claim 1 wherein said amount of said compound is further limited to an oral amount of about 0.5 g/kg of body weight/day to about 2.0 g/kg of body weight/day based on glyceryl tris (3-hydroxybutyrate) and the stoichiometrically equivalent amount of the 3-hydroxybutyroyl group thereto based on said oral amount for the glyceryl 3-hydroxybutyrate esters other than glyceryl tris (3-hydroxybutyrate) assuming complete hydrolysis of the esters, taken as a single dose or divided doses.

7. The method of claim 6 wherein said administration is continued (a) for 2-4 days for a subject presenting with episodic migraine or (b) for a subject presenting with a chronic repetitive migraine history for at least 2 to 4 days beyond the historic chronic repetitive cycle as determined from said subjects medical history or where such history is unknown or unreliable, for about 1 month.

8. The method of claim 1 wherein said ketone body blood plasma level is achieved within the first 6 hours of administration of said glyceryl (3-hydroxybutyrate)ester compound.

9. The method of claim 1 wherein said ketone body blood plasma level is achieved within the first 2 hours of administration of said glyceryl (3-hydroxybutyrate) ter compound.

10. The method of claim 1 wherein said ketone body blood plasma level is achieved within the first hour of administration of said glyceryl (3-hydroxybutyrate)ester compound.

11. The method of claim 1 wherein administration is begun due to the appearance of one or more prodromal symptoms of migraine.

12. The method of claim 1 wherein administration is begun upon presentation of headache.

13. A method of use of a glyceryl tris (3-hydroxybutyrate) ester bulk compound in the management of migraine symptomology, which bulk compound, upon hydrolysis, gives rise to glycerol moieties and 3-hydroxybutyrate moieties in the ratio of 1 glycerol moiety:3 (3-hydroxybutyrate) moieties, comprising:
administering an amount of said glyceryl tris (3-hydroxybutyrate) ester bulk compound
- (a) to a subject presenting with at least one migraine symptom, wherein said amount is sufficient to eliminate, control, limit, or reduce said at least one symptom or
- (b) to a subject so as to prevent the onset of at least one of said symptoms from a previously established pattern of migraine symptom onset, wherein each of the 3-hydroxybutyrate groups in said glyceryl tris (3-hydroxybutyrate) ester bulk compound is independently selected from the D and L form and mixtures thereof;

said amount of said compound which is administered is sufficient to raise the subject's ketone body blood plasma levels, as measured by the subject's combined blood plasma levels of 3-hydroxybutyrate and acetoacetate, to a range having a lower and upper limit selected from 6 mM, 6.5 mM, 7 mM and about 7.5 mM within the first 24 hours of administration of said glyceryl tris (3-hydroxybutyrate) ester bulk compound, provided said upper limit of the range is larger than the lower limit of the range.

14. A method of use of a glyceryl (3-hydroxybutyrate) ester compound in the management of migraine symptomology and which compound, in bulk, upon complete hydrolysis, yields only glycerol and 3-hydroxybutyrate moieties in a ratio of 1 glycerol:3 (3-hydroxybutyrate), comprising:
administering an amount of said compound
- (a) to a subject presenting with at least one migraine symptom, wherein said amount is sufficient to eliminate, control, limit, or reduce said at least one symptom or
- (b) to a subject so as to prevent the onset of at least one of said symptoms from a previously established pattern of migraine symptom onset wherein each of the 3-hydroxybutyrate groups in said compound is independently selected from the D and L form and mixtures thereof;

said amount of said compound which is administered is sufficient to raise the subject's ketone body blood plasma levels, as measured by the subject's combined blood plasma levels of 3-hydroxybutyrate and acetoacetate, to a range having a lower and upper limit selected from 6 mM, 6.5 mM, 7 mM and about 7.5 mM within the first 24 hours of administration of said compound, provided said upper limit of the range is larger than the lower limit of the range.

\* \* \* \* \*

UNITED STATES PATENT AND TRADEMARK OFFICE
CERTIFICATE OF CORRECTION

PATENT NO. : 10,792,269 B2
APPLICATION NO. : 16/220365
DATED : October 6, 2020
INVENTOR(S) : Hashim It is certified that error appears in the above-identified patent and that said Letters Patent is hereby corrected as shown below:

In the Specification

Column 1, Line 53, replace "blood" with "blood plasma".

Column 4, Line 18, replace "blood" with "blood plasma".

Column 4, Line 45, replace "blood" with "blood plasma".

Column 6, Line 52, replace "blood" with "blood plasma".

Column 8, Line 17, replace "2.0 S/kg" with "2.0 g/kg".

Column 8, Line 21, replace "blood" with "blood plasma".

Column 8, Line 50, replace "blood" with "blood plasma".

Column 9, Line 59, replace "blood" with "blood plasma".

Signed and Sealed this
Tenth Day of November, 2020

Andrei Iancu
*Director of the United States Patent and Trademark Office*